(12) United States Patent
Zeledon et al.

(10) Patent No.: US 10,874,457 B2
(45) Date of Patent: Dec. 29, 2020

(54) SEGMENTED GROUND PADS FOR ELECTROPHYSIOLOGY SYSTEMS

(71) Applicant: Cardiac Pacemakers, Inc., St. Paul, MN (US)

(72) Inventors: Esteban Martin Solorzano Zeledon, Desamparados (CR); Adrian Valdelomar, La Guacima (CR)

(73) Assignee: Cardiac Pacemakers, Inc., St Paul, MN (US)

( * ) Notice: Subject to any disclaimer, the term of this patent is extended or adjusted under 35 U.S.C. 154(b) by 592 days.

(21) Appl. No.: 15/716,096

(22) Filed: Sep. 26, 2017

(65) Prior Publication Data

US 2018/0085163 A1    Mar. 29, 2018

Related U.S. Application Data

(60) Provisional application No. 62/400,556, filed on Sep. 27, 2016.

(51) Int. Cl.
*A61B 18/12* (2006.01)
*A61B 18/16* (2006.01)
(Continued)

(52) U.S. Cl.
CPC .......... *A61B 18/16* (2013.01); *A61B 18/1492* (2013.01); *A61B 34/20* (2016.02);
(Continued)

(58) Field of Classification Search
CPC ................ A61B 18/1492; A61B 18/16; A61B 2017/00199; A61B 2017/0023;
(Continued)

(56) References Cited

U.S. PATENT DOCUMENTS 3,895,635 A * 7/1975 Justus .................. A61B 5/0424
606/32
5,496,363 A   3/1996 Burgio et al.
(Continued)

FOREIGN PATENT DOCUMENTS

EP       2942023 A2    11/2015
WO    2005110263 A2    11/2005

OTHER PUBLICATIONS

Jain, Mudit K.; et al. "Effect of Skin Electrode Location on RadioFrequency Ablation Lesions: An In Vivo and a Three-Dimensional Finite Element Study." Journal of Cardiovascular Electrophysiology, 9(12):1325-1335, Dec. 1998.
(Continued)

*Primary Examiner* — Daniel W Fowler
(74) *Attorney, Agent, or Firm* — Faegre Drinker Biddle & Reath LLP (57) ABSTRACT

Segmented ground pads for electrophysiology systems are disclosed. In an embodiment, a ground pad array system for use with an electrophysiology system comprises: a ground pad comprising a plurality of conductive segments, wherein each conductive segment is capable of being independently activated. The embodiment also includes a plurality of conductive wires coupled to the plurality of conductive segments and a switching apparatus. The switching apparatus is configured to activate one or more conductive segments, wherein the ground pad strip provides a ground path for energy emitted by a catheter of the electrophysiology system, in response to the activation of the one or more conductive segments.

14 Claims, 7 Drawing Sheets

(51) Int. Cl.
*A61B 34/20* (2016.01)
*A61B 18/14* (2006.01)
A61B 18/00 (2006.01)
A61B 17/00 (2006.01)

(52) U.S. Cl.
CPC ............... *A61B 2017/0023* (2013.01); *A61B 2017/00199* (2013.01); *A61B 2018/0016* (2013.01); *A61B 2018/00351* (2013.01); *A61B 2018/00577* (2013.01); *A61B 2018/00654* (2013.01); *A61B 2018/00708* (2013.01); *A61B 2018/00779* (2013.01); *A61B 2018/00791* (2013.01); *A61B 2018/00875* (2013.01); *A61B 2018/165* (2013.01)

(58) Field of Classification Search
CPC .. A61B 2018/0016; A61B 2018/00351; A61B 2018/00577; A61B 2018/00654; A61B 2018/00708; A61B 2018/00779; A61B 2018/00791; A61B 2018/00875; A61B 2018/165; A61B 34/20
See application file for complete search history.

(56) References Cited

U.S. PATENT DOCUMENTS

| | | | |
|---|---|---|---|
| 5,575,766 A * | 11/1996 | Swartz | A61M 25/0041 600/16 |
| 2002/0065455 A1 * | 5/2002 | Ben-Haim | A61N 1/36564 600/407 |
| 2003/0045871 A1 * | 3/2003 | Jain | A61B 18/1206 606/41 |
| 2007/0049914 A1 | 3/2007 | Eggleston | |
| 2007/0049919 A1 * | 3/2007 | Lee, Jr. | A61B 18/1233 606/34 |
| 2009/0187177 A1 | 7/2009 | Epstein | |
| 2011/0264000 A1 | 10/2011 | Paul et al. | |
| 2014/0100562 A1 | 4/2014 | Sutermeister et al. | |
| 2015/0320478 A1 | 11/2015 | Cosman, Jr. et al. | |
| 2015/0351831 A1 | 12/2015 | Janssen et al. | |

OTHER PUBLICATIONS

Schutt, David J.; et al. "Sequential Activation of a Segmented Ground Pad Reduces Skin Heating During Radiofrequency Tumor Ablation: Optimization via Computational Models." IEEE Trans Biomed Eng. Author manuscript: available in PMC Jul. 16, 2009 pp. 1-28.

Schutt, David J.; et al. "Sequential Activation of Ground Pads Reduces Skin Heating During Radiofrequency Tumor Ablation: In Vivo Porcine Results," IEEE Transactions On Biomedical Engineering, 57(3):746-753, Mar. 2010.

International Search Report and Written Opinion issued in PCT/US2017/053507, dated Dec. 20, 2017, 16 pages.

* cited by examiner

SEGMENTED GROUND PADS FOR ELECTROPHYSIOLOGY SYSTEMS

CROSS-REFERENCE TO RELATED APPLICATION

This application claims priority to Provisional Application No. 62/400,556, filed Sep. 27, 2016, which is herein incorporated by reference in its entirety.

TECHNICAL FIELD

The present disclosure relates to electrophysiology systems. More specifically, the present disclosure relates to systems, methods, and devices for diagnosis and ablation of tissue using a segmented ground pad.

BACKGROUND

In ablation therapy, a physician may ablate different abnormal tissue to either stun or induce a permanent lesion. In interventional cardiac electrophysiology procedures, for example, it is often necessary for the physician to determine the condition of cardiac tissue at a target ablation site in or near the heart.

SUMMARY

Embodiments of the present disclosure relate to segmented ground pads for electrophysiology systems. Example embodiments include the following.

In an Example 1, a ground pad array system for use with an electrophysiology system, the ground pad array system comprises: a ground pad comprising a plurality of conductive segments, wherein each conductive segment is capable of being independently activated; a plurality of conductive wires coupled to the plurality of conductive segments and a switching apparatus, wherein the switching apparatus is configured to activate one or more conductive segments, and wherein the ground pad strip provides a ground path for energy emitted by a catheter of the electrophysiology system, in response to the activation of the one or more conductive segments.

In an Example 2, the ground pad array system of Example 1, wherein the ground pad comprises: a reusable portion comprising a plurality of contacts, wherein each contact is configured to be removably coupled to a respective conductive segment; and a disposable portion comprising the plurality of conductive segments.

In an Example 3, the ground pad array system of any of Examples 1 and 2, wherein the plurality of conductive segments are arranged in a Cartesian coordinate grid or a polar coordinate grid.

In an Example 4, the ground pad array system of any of Examples 1-3, wherein the ground pad array system further comprises a processor communicatively coupled to the switching apparatus, wherein the processor is configured to: receive a location of the catheter's distal tip; and send a signal to the switching apparatus to activate the one or more conductive segments based on the location of the catheter's distal tip.

In an Example 5, the ground pad array system of Example 4, wherein the one or more activated conductive segments is a proper subset of the plurality of conductive segments.

In an Example 6, the ground pad array system of any of Examples 4 and 5, wherein the received location of the catheter's distal tip comprises an orientation of the catheter's distal tip and a position of the catheter's distal tip.

In an Example 7, the ground pad array system of any of Examples 3-6, wherein the processor is configured to: receive a change in location of the catheter's distal tip; and send a signal to the switching apparatus to modify the one or more activated conductive segments based on the change in location of the catheter's distal tip.

In an Example 8, the ground pad array system of any of Examples 3-7, wherein to send a signal to the switching apparatus to activate the one or more conductive segments based on the location of the catheter's distal tip, the processor is configured to: determine a number of the plurality of conductive segments to be activated; determine at least one conductive segment that is located closest to the location of the catheter's distal tip; and send a signal to the switching apparatus to activate the determined number of the plurality of conductive segments, wherein locations of the activated conductive segments is approximately centered at the at least one determined conductive segment that is located closest to the location of the catheter's distal tip.

In an Example 9, the ground pad array system of Example 9, wherein to determine a number of plurality of conductive segments to be activated, the processor is configured to: determine a preferred energy per unit area; and determine the number of the plurality of conductive segments to be activated based on the determined preferred energy per unit area.

In an Example 10, the ground pad array system of Example 10, wherein to determine a preferred energy per unit area, the processor is configured to: determine an impedance sensed by the catheter; and determine the preferred energy per unit area based on the determined impedance.

In an Example 11, the ground pad array system of any of Examples 9-10, wherein to determine a preferred energy per unit area, the processor is configured to: determine a temperature sensed by the catheter; and determine the preferred energy per unit area based on the determined temperature.

In an Example 12, a method comprises: receiving a location of a catheter's distal tip of an electrophysiology system; and activating one or more conductive segments of a plurality of conductive segments of a ground pad array system, to provide a ground path for energy emitted by the catheter, based on the location of the catheter's distal tip, wherein each conductive segment is capable of being independently activated.

In an Example 13, the method of Example 12, further comprising: receiving a change in location of the catheter's distal tip; and updating the one or more activated conductive segments based on the change in location of the catheter's distal tip.

In an Example 14, the method of any of Examples 11-12, further comprising: determining a number of the plurality of conductive segments to be activated; determining at least one conductive segment that is located closest to the location of the catheter's distal tip; and activating the determined number of the plurality of conductive segments, wherein locations of the activated conductive segments is approximately centered at the at least one determined conductive segment that is located closest to the location of the catheter's distal tip.

In an Example 15, the method of Example 14, wherein determining a number of the plurality of conductive segments to be activated comprises: determining an impedance sensed by the catheter; determining a preferred energy per unit area based on the determined impedance; and determining the number of the plurality of conductive segments to be activated based on the determined preferred energy per unit area.

In an Example 16, a system comprises: a ground pad comprising a plurality of conductive segments, wherein each conductive segment is capable of being independently activated; a plurality of conductive wires coupled to the plurality of conductive segments; a switching apparatus coupled to the plurality of conductive wires; and a processor coupled to the switching apparatus, wherein the processor is configured to send a signal to the switching apparatus to activate one or more conductive segments in order to provide a ground path for energy emitted by an catheter of an electrophysiology system.

In an Example 17, the system of Example 16, wherein the ground pad comprises: a reusable portion comprising a plurality of contacts, wherein each contact is configured to be removably coupled to a respective conductive segment; and a disposable portion comprising the plurality of conductive segments.

In an Example 18, the system of Example 16, wherein the plurality of conductive segments are arranged in a Cartesian coordinate grid or a polar coordinate grid.

In an Example 19, the system of Example 16, wherein to send a signal to the switching apparatus to activate one or more conductive segments, the processor is configured to: receive a location of the catheter's distal tip; and send the signal to the switching apparatus to activate the one or more conductive segments based on the location of the catheter's distal tip.

In an Example 20, the system of Example 19, wherein the one or more activated conductive segments is a proper subset of the plurality of conductive segments.

In an Example 21, the system of Example 19, wherein the received location of the catheter's distal tip comprises an orientation of the catheter's distal tip and a position of the catheter's distal tip.

In an Example 22, the system of Example 19, wherein the processor is configured to: receive a change in location of the catheter's distal tip; and send a signal to the switching apparatus to modify the one or more activated conductive segments based on the change in location of the catheter's distal tip.

In an Example 23, the system of Example 19, wherein to send a signal to the switching apparatus to activate the one or more conductive segments based on the location of the catheter's distal tip, the processor is configured to: determine a number of the plurality of conductive segments to be activated; determine at least one conductive segment that is located closest to the location of the catheter's distal tip; and send a signal to the switching apparatus to activate the determined number of the plurality of conductive segments, wherein locations of the activated conductive segments is approximately centered at the at least one determined conductive segment that is located closest to the location of the catheter's distal tip.

In an Example 24, the system of Example 23, wherein to determine a number of plurality of conductive segments to be activated, the processor is configured to: determine a preferred energy per unit area; and determine the number of the plurality of conductive segments to be activated based on the determined preferred energy per unit area.

In an Example 25, the system of Example 24, wherein to determine a preferred energy per unit area, the processor is configured to: determine an impedance sensed by the catheter; and determine the preferred energy per unit area based on the determined impedance.

In an Example 26, the system of Example 24, wherein to determine a preferred energy per unit area, the processor is configured to: determine a temperature sensed by the catheter; and determine the preferred energy per unit area based on the determined temperature.

In an Example 27, a method comprises: receiving a location of a catheter's distal tip of an electrophysiology system; and activating one or more conductive segments of a plurality of conductive segments of a ground pad array system, to provide a ground path for energy emitted by the catheter, based on the location of the catheter's distal tip, wherein each conductive segment is capable of being independently activated.

In an Example 28, the method of Example 27, further comprising: receiving a change in location of the catheter's distal tip; and updating the one or more activated conductive segments based on the change in location of the catheter's distal tip.

In an Example 29, the method of Example 27, further comprising: determining a number of the plurality of conductive segments to be activated; determining at least one conductive segment that is located closest to the location of the catheter's distal tip; and activating the determined number of the plurality of conductive segments, wherein locations of the activated conductive segments is approximately centered at the at least one determined conductive segment that is located closest to the location of the catheter's distal tip.

In an Example 30, the method of Example 29, wherein determining a number of the plurality of conductive segments to be activated comprises: determining a preferred energy per unit area; and determining the number of the plurality of conductive segments to be activated based on the determined preferred energy per unit area.

In an Example 31, the method of Example 30, wherein determining a preferred energy per unit area comprises: determining an impedance sensed by the catheter; and determining the preferred energy per unit area based on the determined impedance.

In an Example 32, a ground pad array system for use with an electrophysiology system, the ground pad array system comprising: a ground pad comprising a plurality of conductive segments, wherein each conductive segment is capable of being independently activated; a plurality of conductive wires coupled to the plurality of conductive segments and a switching apparatus, wherein the switching apparatus is configured to activate one or more conductive segments, and wherein the ground pad strip provides a ground path for energy emitted by a catheter of the electrophysiology system, in response to the activation of the one or more conductive segments.

In an Example 33, the ground pad array system of Example 32, wherein the ground pad comprises: a reusable portion comprising a plurality of contacts, wherein each contact is configured to be removably coupled to a respective conductive segment; and a disposable portion comprising the plurality of conductive segments.

In an Example 34, the ground pad array system of Example 32, wherein the plurality of conductive segments are arranged in a Cartesian coordinate grid or a polar coordinate grid.

In an Example 35, the ground pad array system of Example 32, wherein the switching apparatus is configured to activate one or more conductive segments based on a location of a catheter's distal tip of the electrophysiology system.

While multiple embodiments are disclosed, still other embodiments of the present disclosure will become apparent to those skilled in the art from the following detailed description, which shows and describes illustrative embodiments of the disclosed subject matter. Accordingly, the drawings and detailed description are to be regarded as illustrative in nature and not restrictive.

Although the term "block" may be used herein to connote different elements illustratively employed, the term should not be interpreted as implying any requirement of, or particular order among or between, various blocks disclosed herein. Similarly, although illustrative methods may be represented by one or more drawings (e.g., flow diagrams, communication flows, etc.), the drawings should not be interpreted as implying any requirement of, or particular order among or between, various steps disclosed herein. However, certain embodiments may require certain steps and/or certain orders between certain steps, as may be explicitly described herein and/or as may be understood from the nature of the steps themselves (e.g., the performance of some steps may depend on the outcome of a previous step). Additionally, a "set," "subset," or "group" of items (e.g., inputs, algorithms, data values, etc.) may include one or more items, and, similarly, a subset or subgroup of items may include one or more items. A "plurality" means more than one.

DETAILED DESCRIPTION

While the disclosed subject matter is amenable to various modifications and alternative forms, specific embodiments have been shown by way of example in the drawings and are described in detail below. The intention, however, is not to limit the disclosed subject matter to the particular embodiments described. On the contrary, the disclosed subject matter is intended to cover all modifications, equivalents, and alternatives falling within the scope of the disclosed subject matter as defined by the appended claims.

As the terms are used herein with respect to ranges of measurements (such as those disclosed immediately above), "about" and "approximately" may be used, interchangeably, to refer to a measurement that includes the stated measurement and that also includes any measurements that are reasonably close to the stated measurement, but that may differ by a reasonably small amount such as will be understood, and readily ascertained, by individuals having ordinary skill in the relevant arts to be attributable to measurement error, differences in measurement and/or manufacturing equipment calibration, human error in reading and/or setting measurements, adjustments made to optimize performance and/or structural parameters in view of differences in measurements associated with other components, particular implementation scenarios, imprecise adjustment and/or manipulation of objects by a person or machine, and/or the like.

Various cardiac abnormalities can be attributed to improper electrical activity of cardiac tissue. Such improper electrical activity can include, but is not limited to, generation of electrical signals, conduction of electrical signals, and/or compression of the tissue in a manner that does not support efficient and/or effective cardiac function. For example, an area of cardiac tissue may become electrically active prematurely or otherwise out of sync during the cardiac cycle, causing the cardiac cells of the area and/or adjacent areas to contract out of rhythm. The result is an abnormal cardiac contraction that is not timed for optimal cardiac output. In some cases, an area of cardiac tissue may provide a faulty electrical pathway (e.g., a short circuit) that causes an arrhythmia, such as atrial fibrillation or supraventricular tachycardia. In some cases, inactive tissue (e.g., scar tissue) may be preferable to malfunctioning cardiac tissue.

Cardiac ablation is a procedure by which cardiac tissue is treated to inactivate the tissue. The tissue targeted for ablation may be associated with improper electrical activity, as described above. Cardiac ablation can lesion the tissue and prevent the tissue from improperly generating or conducting electrical signals. For example, a line, a circle, or other formation of ablated cardiac tissue can block the propagation of errant electrical signals. In some cases, cardiac ablation is intended to cause the death of cardiac tissue and to have scar tissue reform over the lesion, where the scar tissue is not associated with the improper electrical activity. Ablation therapies include radiofrequency (RF) ablation, cyroablation, microwave ablation, laser ablation, and surgical ablation, among others.

During RF ablation, a catheter emits RF energy to lesion the diseased cardiac tissue of a patient. A ground pad, attached to the patient, provides a ground for the RF energy emitted from the RF catheter. Conventional RF ablation implementations, however, use a ground pad that may result in excess RF energy being emitted into untargeted cardiac tissue and/or into the blood of the patient. As a result, the untargeted cardiac tissue may be ablated and/or the temperature of the patient's blood may rise, both of which are undesirable and may result in adverse events for the patient. The embodiments provided herein may reduce the amount of RF energy emitted into untargeted tissue and/or into patient's blood, as described below. In embodiments, since the RF energy being emitted into untargeted tissue may be reduced, the effectiveness of the RF energy that is delivered to the tissue may be increased and/or less RF energy may be lost due to impedance.

For purposes of illustration, and not of limitation, various embodiments disclosed herein are described in the context of cardiac electrophysiology systems. However, the embodiments disclosed herein may be used in other electrophysiology systems and on organs other than the heart.

Figure 1:
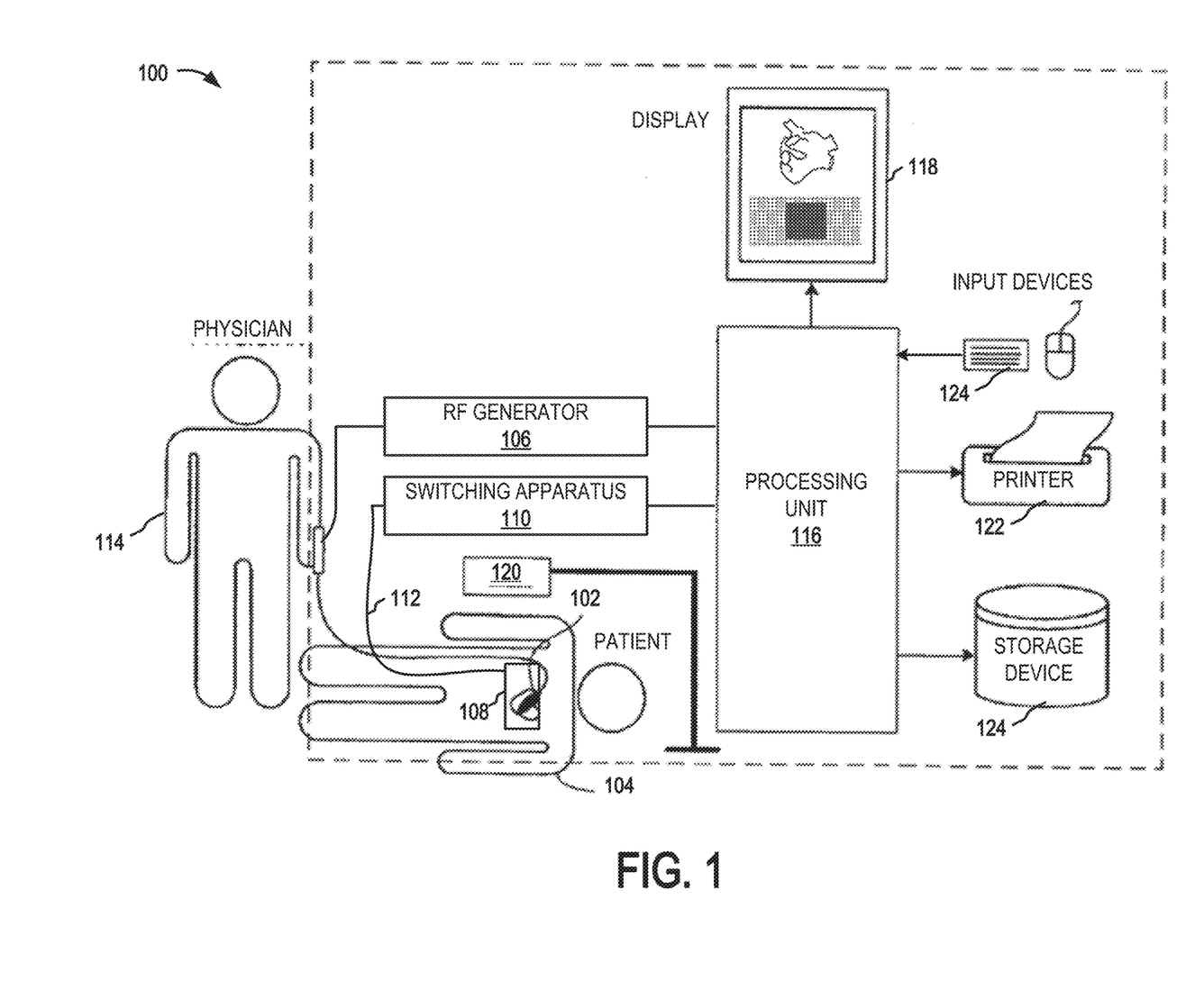
FIG. 1 is a conceptual diagram depicting an illustrative electrophysiology system using a segmented ground pad, in accordance with embodiments of the present disclosure.

FIG. 1 is a conceptual diagram depicting an illustrative electrophysiology system 100, in accordance with embodiments of the present disclosure. The electrophysiology system 100 includes a moveable catheter 102 having one or more ablation electrodes coupled to the tip of the catheter 102. The tip of the catheter 102 may be deployed into a patient's 104 heart for ablative procedures. To allow deployment into the heart, the electrodes of the catheter 102 may be mounted on an actuable structure to control movement of the catheter's 102 tip.

In operation, a user positions the ablation electrode of the catheter 102 to contact targeted cardiac tissue of a patient 104. An RF generator 106 may generate ablative energy that is transported to the catheter 102 via one or more wires. In embodiments, the RF energy generated by the RF generator 106 may have a frequency of approximately between 300 to 3000 kHz. The RF energy received by the catheter 102, from the RF generator 106, is conducted by an ablation electrode of the catheter 102 through cardiac tissue to a segmented ground pad 108. The RF energy is at least partially dissipated as heat in the cardiac tissue. The heat dissipated in the cardiac tissue is sufficient enough to form a lesion on the cardiac tissue. The formed lesion can treat cardiac rhythm disturbances and/or abnormalities, as described above.

As previously stated, the RF energy is conducted by the ablation electrode of the catheter 102 to a segmented ground pad 108. The ground pad 108, as disclosed herein, includes a plurality of segments that are configured to be activated independently of one another by a switching apparatus 110. That is, one or more wires of a plurality of wires 112 are coupled to respective segments of the ground pad 108; and, the switching apparatus 110 includes one or more switches (e.g., solid state relays, transistors and/or the like) that are coupled to respective wires of the plurality of wires 112. Each of the one or more switches of the switching apparatus 110 may be independently closed to activate the respective segment and, therefore, form a completed circuit so that current can flow from the ablation electrode of the catheter 102 to the respective segment of the ground pad 108. Alternatively, when one or more switches coupled to a respective segment of the ground pad 108 are open, the respective segment will not be activated and, therefore, a completed circuit will not be formed. Therefore, current will not flow to the respective segment of the ground pad 108 that has the respective one or more open switches coupled thereto. Due to this configuration, different segments of the ground pad 108 are capable of being activated independently. Potential benefits of this implementation are discussed below in relation to FIGS. 2A-2C.

In embodiments, the catheter 102 may also be used to map the patient's 104 heart. During a mapping stage, the catheter 102 is displaced to multiple locations within the heart chamber of the patient 104. In some embodiments the distal end of the catheter 102 includes multiple mapping electrodes. At each of the locations to which the catheter 102 is moved, the catheter's 102 multiple mapping electrodes acquire signals resulting from the electrical activity in the heart. A map of the heart and the heart's electrical activity may be reconstructed and presented to a user 114 (such as a physician and/or technician) based on the signals acquired at multiple locations by the mapping electrodes.

The electrophysiology system 100 further includes a processing unit 116 which performs several of the operations pertaining to the ablation and/or mapping procedures. For example, the processing unit 116 sends signals to the switching apparatus 110 indicative of which segments of the ground pad 108 should be activated. As another example, the processing unit 116 generates a display, on a display device 118, of one or more of the following: the activated segments of the ground pad 108, the mapped heart chamber and/or the catheter's 102 location relative to the surface of the heart chamber.

In embodiments, the location of the catheter 102 inserted into the heart chamber may be determined using a tracking system 120. The tracking system 120 may provide 3D spatial coordinates of the catheter 102 and/or its multiple electrodes with respect to a coordinate system (e.g., the catheter's coordinate system). The 3D spatial locations of the catheter 102 may be correlated to 3D spatial coordinates of the cardiac chamber of the patient 104 to determine a position of the catheter 102 and/or orientation of the catheter's 102 tip relative to the cardiac chamber.

Embodiments of the tracking system 120 may use hybrid location technology that combines impedance, magnetic location technology and/or force sensing to determine the 3D spatial coordinates of the catheter 102 and/or its multiple electrodes. Magnetic location technology uses magnetic fields, generated by a localization generator positioned under the patient table, to track catheters with magnetic sensors. Impedance location technology may be used to track catheters that may not be equipped with a magnetic location sensor, and may utilize surface ECG patches. Force sensing technology may use force sensors disposed on the tip of the catheter 102 to determine the force exerted on the catheter's 102 tip and, therefore, an orientation of the catheter 102 relative to a surface of the cardiac chamber.

As illustrated in FIG. 1, the electrophysiology system 100 may also include peripheral devices in addition to, or alternatively to, the display device 118, such as a printer 122 and/or input devices 124 (e.g., a mouse, keyboard, touchscreen and/or the like), which may be interconnected to the processing unit 116. In embodiments, the electrophysiology system 100 may include a storage device 124 that may be used to store algorithms utilized by the processing unit 116 including, for example, activation algorithms for the segmented ground pad 108, as described below. In embodiments, the storage device 124 may also be used to store data acquired by the catheter 102.

The illustrative electrophysiology system 100 shown in FIG. 1 is not intended to suggest any limitation as to the scope of use or functionality of embodiments of the present disclosure. Neither should the illustrative electrophysiology system 100 be interpreted as having any dependency or requirement related to any single component or combination of components illustrated therein. Additionally, various components depicted in FIG. 1 may be, in embodiments, integrated with various other components depicted therein (and/or components not illustrated), all of which are considered to be within the ambit of the present disclosure. For example, the storage device 124 may be incorporated into the processing unit 116.

As stated above, conventional RF ablation implementations use a ground pad that can result in excess RF energy being emitted into untargeted cardiac tissue and/or into the blood of the patient. That is, conventional ground pads generally comprise a large dispersive electrode. The large dispersive electrode of a conventional ground pad receives energy emitted by the ablation electrode of a catheter. The conduction of the RF energy from the ablation electrode through the cardiac tissue to the ground pad travels the path of least resistance. In embodiments, however, the path of least resistance may not be the path having the shortest distance. This may be due to some portions of cardiac tissue (e.g., thicker portions of cardiac tissue) having higher impedances than other portions of cardiac tissue (e.g., thinner portions of cardiac tissue). Accordingly, if the path of least resistance is not the path having the shortest distance, the RF energy emitted by the ablation electrode may be conducted through untargeted tissue and/or blood.

Figure 2A:
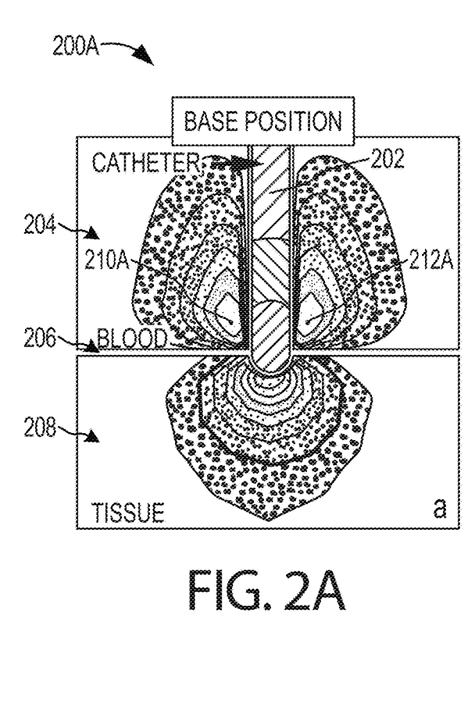
FIGS. 2A-2C are illustrations depicting electromagnetic energy delivery maps for different conduction paths of RF energy emitted by a catheter, in accordance with embodiments of the present disclosure.
Figure 2B:
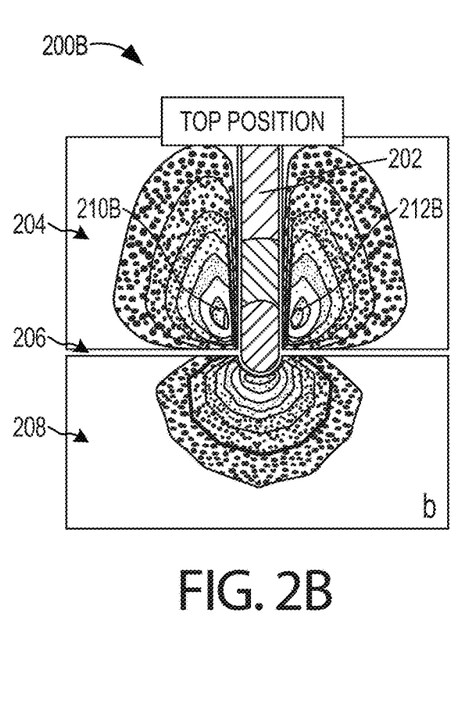
Figure 2C:
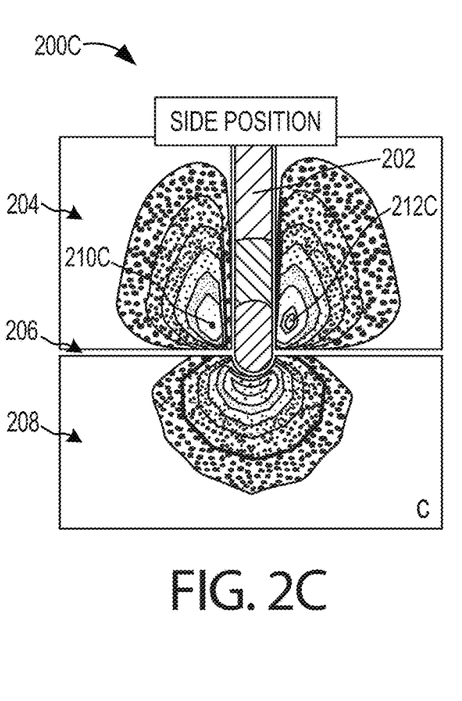

FIGS. 2A-2C are illustrations depicting electromagnetic energy delivery maps 200A-200C for different conduction paths of RF energy emitted by a catheter 202, in accordance with embodiments of the present disclosure. The conduction path of the RF energy being emitted by the catheter 202 is travelling to a ground pad (not shown). Each FIG. of FIGS. 2A-2C, however, depicts an electromagnetic energy delivery map for a respective conduction path. The different conduction paths are due to the RF energy being received by different portions of the ground pad.

As illustrated in FIGS. 2A-2C, the catheter 202 is disposed in the blood 204 of a cardiac chamber. The tip of the catheter 202 is touching the endocardium surface 206 of the cardiac chamber and RF energy emitted by the catheter 202 is conducted into the blood 204, the endocardium surface 206 and cardiac tissue 208. In embodiments, the catheter 202 may have some or all of the same characteristics as the catheter 102 depicted in FIG. 1.

FIG. 2A depicts a conduction path that travels approximately the shortest distance from the tip of the catheter 202 to the ground pad. FIGS. 2B and 2C depict conduction paths that travel longer distances than the shortest distance from the tip of the catheter 202 to the ground pad. From the illustrated perspective of FIG. 2B, the portion of the ground pad receiving the RF energy is located either anterior to or posterior to the portion of the ground pad that is closest to the tip of the catheter 202, which results in the longer conduction path. From the illustrated perspective of FIG. 2C, the portion of the ground pad receiving the RF energy is located to the right of the tip of the catheter 202, which results in the longer conduction path. The different conduction path lengths of FIGS. 2A-2C result in different temperatures increases for the blood 204 and cardiac tissue 208.

That is, due to the conduction path traveling approximately the shortest distance to the ground pad in FIG. 2A, the temperature increase of the blood 204 surrounding the catheter 202 is smaller than the temperature increase of the blood 204 surrounding the catheter 202 in FIGS. 2B and 2C. For example, the portions 210A, 212A of the blood 204 have a smaller temperature increases than the portions 210B, 212B, 212C of the blood 204. Blood coagulation is less likely with a smaller increase in temperature, which is beneficial for a patient. Moreover, when the conduction path travels approximately the shortest distance from the catheter 202 to the ground pad, more RF energy is conducted into the cardiac tissue 208, which results in better, more predictable lesion formation.

To facilitate a conduction path that travels the shortest distance from the tip of the catheter 202 to the ground pad, a segment of the ground pad (e.g., the segmented ground pad 108 depicted in FIG. 1) that is located closest to the location of the tip of the catheter 202 may be activated. Accordingly, when segment of the ground pad is activated that is located closest to the tip of the catheter 202, a conduction path similar to the conduction path of FIG. 2A may result. On the contrary, the longer conduction paths of FIGS. 2B and 2C may result from using conventional ground pads. That is, different cardiac impedances, which result in varying cardiac impedances, may result in paths of least resistance to a conventional ground pad that are longer than the path having the shortest distance.

Figure 3:
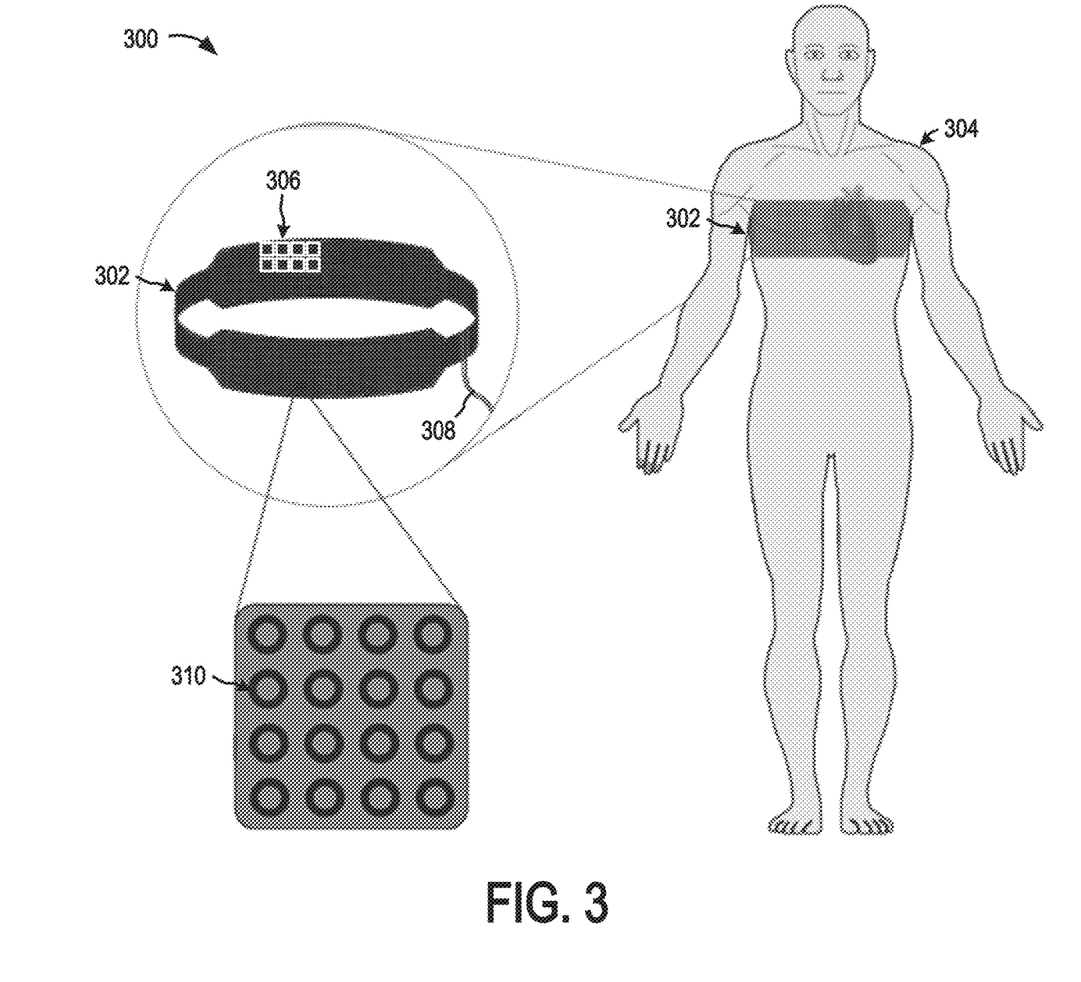
FIG. 3 is a conceptual diagram depicting an illustrative segmented ground pad attached to a user, in accordance with embodiments of the present disclosure.

FIG. 3 is a conceptual diagram 300 depicting an illustrative segmented ground pad 302 attached to a patient 304, in accordance with embodiments of the present disclosure. As described above, the ground pad 302 is attached to a patient 304 and receives energy emitted from an ablation electrode of a catheter (e.g., the catheter 102 depicted in FIG. 1 and/or the catheter depicted in FIG. 2). Further, the ground pad 302 includes a plurality of conductive segments 306. Each conductive segment 306 is capable of being activated independently, via one or more respective wires of a plurality of wires 308 coupled to a respective conductive segment 306 and a switching apparatus (e.g., the switching apparatus 110 depicted in FIG. 1). When a segment 306 is activated, the segment 306 completes a circuit for the RF energy that is emitted by an ablation electrode of a catheter, as described above in relation to FIG. 1. While the illustrated embodiment depicts only a portion of the ground pad 302 including eight conductive segments, in embodiments, the entire ground pad 302 may include conductive segments. Further, in embodiments, the size of the conductive segments 306 may be smaller or larger than the conductive segments 306 depicted in FIG. 3.

In embodiments, the ground pad 302 may include a reusable portion and a non-reusable portion. The reusable portion may include a plurality of contacts 310 coupled to one or more respective wires of the plurality of wires 308. The non-reusable portion may include a plurality of conductive segments 306. Each conductive segment of the plurality of conductive segment 306 may be removably coupled to a respective contact of the plurality of contacts 310 by, for example, a socket, pogo pin, land grid array and/or the like. The non-reusable portion, which is the portion that contacts the patient 304, may be peeled from the reusable portion and discarded after use to prevent cross contamination from one patient 304 to another.

Figure 4A:
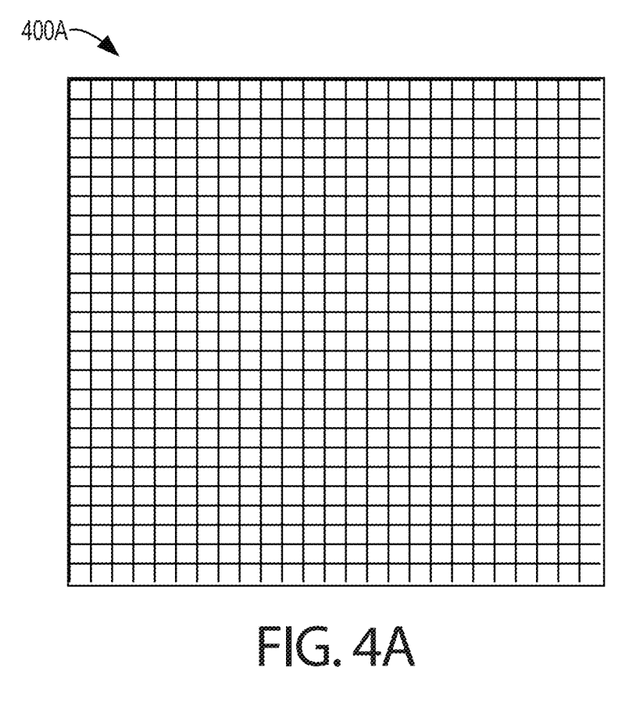
FIGS. 4A-4B illustrate two different patterns of conductive segments for a segmented ground pad, in accordance with embodiments of the present disclosure.
Figure 4B:
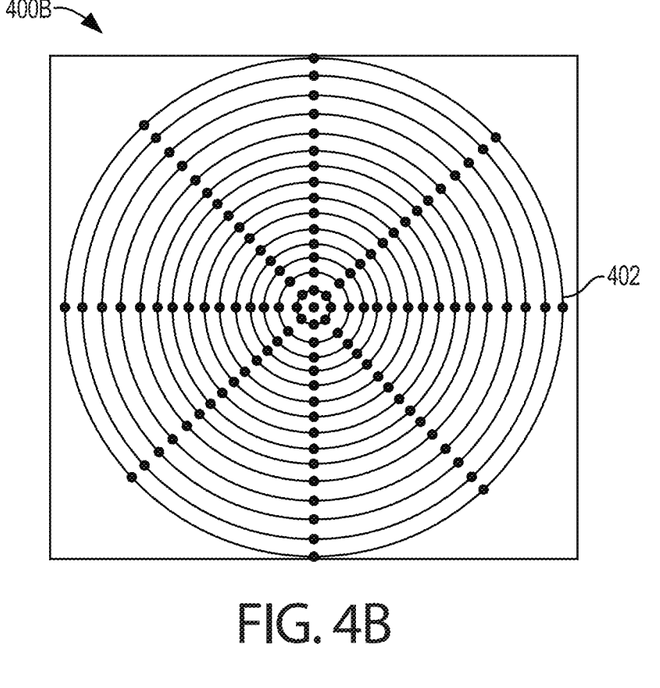

In embodiments, the conductive segments may be arranged in different patterns. FIGS. 4A-4B are two different example patterns of conductive segments for a segmented ground pad, in accordance with embodiments of the present disclosure. FIG. 4A depicts a Cartesian grid 400A. In embodiments, each square or intersection of the Cartesian grid 400A may be a conductive segment that can be independently activated by a switching apparatus (e.g., the switching mechanism 110 depicted in FIG. 1) via one or more wires (e.g., the wires 112 depicted in FIG. 1). FIG. 4B depicts a polar coordinate grid 400B. In embodiments, each point 402 may be a conductive segment that can independently activated by a switching apparatus via one or more wires. However, these are only examples and not meant to be limiting.

Figure 5:
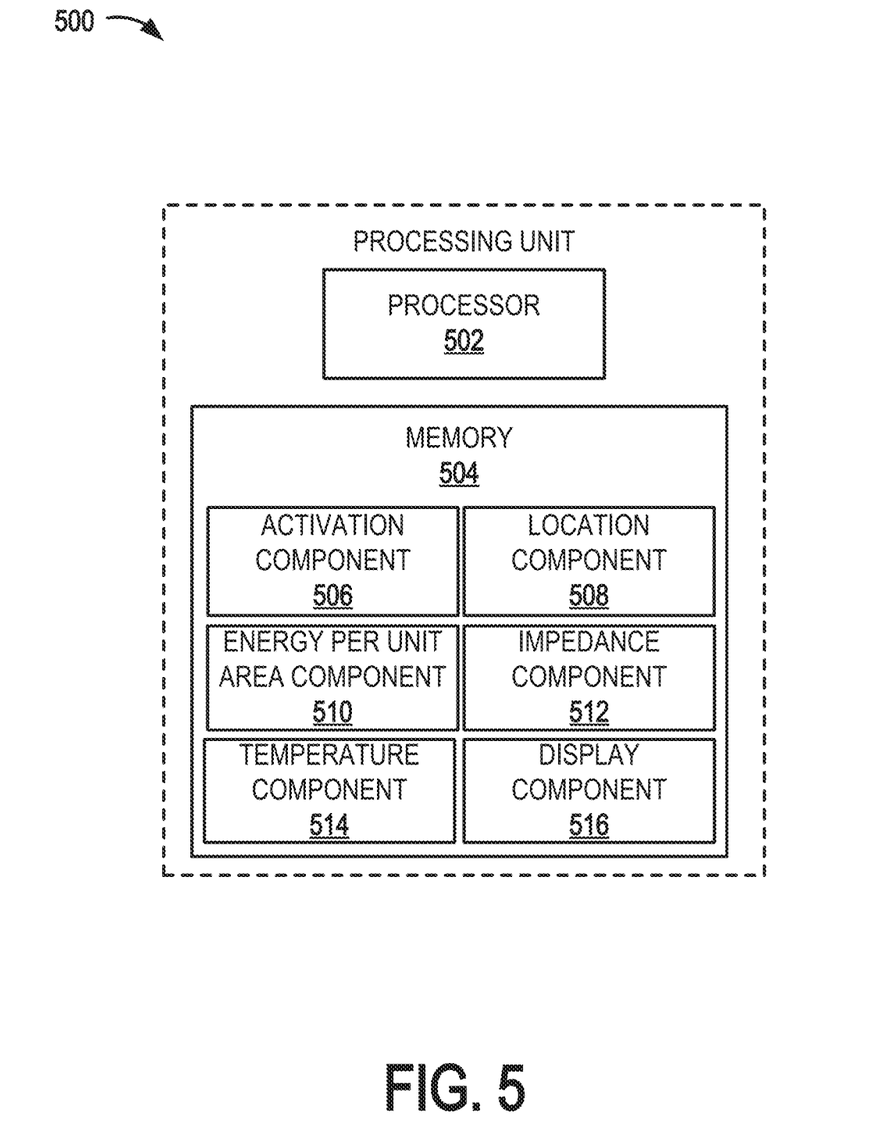
FIG. 5 is a block diagram of an illustrative processing unit for use with an electrophysiology system, in accordance with embodiments of the present disclosure.

FIG. 5 is a block diagram of an illustrative processing unit 500 for use with an electrophysiology system, in accordance with embodiments of the present disclosure. The processing unit 500 may be, be similar to, include, or be included in the processing unit 116 depicted in FIG. 1. As illustrated, the processing unit 500 may be implemented on a computing device that includes a processor 502 and memory 504. Although the processing unit 500 is referred to herein in the singular, the processing unit 500 may be implemented in multiple instances (e.g., as a server cluster), distributed across multiple computing devices, instantiated within multiple virtual machines and/or the like. One or more components 506-516 for facilitating the activation of different segments of a ground pad may be stored in the memory 504. In embodiments, the processor 502 may be configured to instantiate the one or more components 506-516 stored in memory to facilitate the activation of one or more segments of a segmented ground pad (e.g., the segmented ground pad 108 depicted in FIG. 1 and/or the segmented ground pad 302 depicted in FIG. 3). The processor 502 may be, include, or be included in, an electrical processor, a software processor, a general purpose microprocessor, a special purpose microprocessor, a controller and/or an embedded system and may include a sole processor or one of multiple processors or cores.

In the illustrated embodiment, the processing unit 500 includes an activation component 506. The activation component 506 is configured to send one or more signals to a switching apparatus (e.g., the switching apparatus 110 depicted in FIG. 1). The one or signals sent to the switching apparatus are configured to initiate the switching apparatus to close or open one or more switches of the switching apparatus. In response to the closing or opening of one or more switches of the switching apparatus, different conductive segments of a ground pad are activated. As described above, an activated conductive segment of the ground pad allows current to be conducted through the activated conductive segment and, therefore, conduct received RF energy from a catheter. The activation component 506 may: activate all the conductive segments of the ground pad, activate a proper subset of conductive segments of the ground pad, deactivate all the conductive segments of the ground pad and/or deactivate one or more conductive segments of the ground pad. In embodiments, the activation component 506 may send signals to activate and/or deactivate specific conductive segments of the ground pad based on a location of the tip of the catheter, a desired energy per unit area, a sensed impedance, a sensed temperature, as determined by the location component 508, the energy per unit area component 510, the impedance component 512 and the temperature component 514, respectively. In embodiments, the activation component 506 may change and/or update which conductive segments are activated.

In embodiments, the processing unit 500 includes a location component 508. The location component 508 is configured to receive signals from a tracking system (e.g., the tracking system 120). From the received signals, the location component 508 can determine 3D spatial coordinates of the catheter. In embodiments, the location component 508 may also determine the 3D spatial coordinates of a cardiac chamber in which the catheter is disposed. The location component 508 may correlate the 3D spatial coordinates of the catheter to the 3D spatial coordinates of the cardiac chamber of the patient 104 to determine a position of the catheter 102 and/or orientation of the catheter's 102 tip relative to the cardiac chamber. Based on the location of the catheter, as determined by the location component 508, the activation component 506 may activate a conductive segment that is located closest to the tip of the catheter. In embodiments where the activation component 506 activates more than one conductive segment, the activation component may activate a plurality of conductive segments such that the center of the plurality of conductive segments (e.g., a mean center and/or a mean weighted center) has a location that is closest to the tip of the catheter. Additionally or alternatively, in embodiments, if the location component 508 determines a change in location (e.g., due to movement of the ablation catheter, movement of the cardiac tissue due to pumping of the heart, movement of the patient and/or other perturbations that induce movement of the catheter), the activation component 506 may update and/or change the activated conductive segments so that the center of the plurality of activated conductive segments are located closest to the new location of the tip of the catheter.

In embodiments, the processing unit 500 includes an energy per unit area component 510. The energy per unit area component 510 may determine a desired energy per unit area for the ablation procedure and/or for a specific moment of the ablation procedure. These embodiments may be advantageous because different physicians may have different ablation techniques that utilize different energies per unit area for the ablation procedure. For example, some physicians may prefer to focus the energy emitted from the catheter over a larger area of cardiac tissue for a longer period of time. In these embodiments, the energy per unit area component 510 may determine how many conductive segments of the ground pad should be activated to achieve the desired energy per unit area. Alternatively, some physicians may prefer to focus the energy emitted from the catheter over a smaller area cardiac tissue for a shorter period of time. Similarly, in these embodiments, the energy per unit area component 510 may determine how many conductive segments of the ground pad should be activated by the activation component 506 to achieve the desired energy per unit area.

Additionally or alternatively, in some embodiments, physicians may prefer to focus the energy emitted from the catheter over a smaller area of cardiac tissue during a first portion of an ablation procedure and over a larger area of cardiac tissue during a second portion of an ablation procedure. For example, when an ablation procedure commences, the impedance of cardiac tissue may be less than the impedance of the same cardiac tissue at a later time of the ablation procedure. As such, a physician may want to focus the energy emitted by the catheter on a smaller portion of the cardiac tissue when the impedance of the cardiac tissue is low, so that the cardiac tissue is heated to a sufficient level, despite the lower impedance and, therefore, the lower absorption of the RF energy by the cardiac tissue. To do so, the energy per unit area component 510 may determine how many conductive segments of the ground pad should be activated by the activation component 506 to achieve the desired energy per unit area during an initial portion of the ablation procedure. Then, as the ablation procedure continues and the impedance of the cardiac tissue increases, the physician may focus the energy emitted by the catheter over a larger area, so that the increase in impedance does not result in an undesired increase in temperature of the cardiac tissue. To do so, the energy per unit area component 510 may determine how many more conductive segments of the ground pad should be activated by the activation component 506 to achieve the desired energy per unit area. In embodiments, sensors on the tip of the catheter may send signals to the impedance component 512 included in the processing unit 500, which can then determine the impedance of the cardiac tissue.

Additionally or alternatively to using impedance to determine which conductive segments of the ground pad should be activated, the temperature of the environment surrounding the distal tip of the catheter may be used to control which conductive segments of the ground pad should be activated by the activation component 506. For example, when an ablation procedure commences, the temperature of the surrounding environment of the distal tip of the catheter may be low. As such, a physician may want to focus the energy emitted by the catheter on a smaller portion of the cardiac tissue when the temperature of the cardiac tissue is low, so that the cardiac tissue is heated to a sufficient level in a desired period of time. To do so, the energy per unit area component 510 may determine how many conductive segments of the ground pad should be activated by the activation component 506 to achieve the desired energy per unit area during an initial portion of the ablation procedure. Then, as the ablation procedure continues and the temperature of the environment surrounding the catheter's distal tip, the physician may focus the energy emitted by the catheter over a larger area, so that the increase in temperature does not result in an undesired effect on the cardiac tissue, such as popping or searing of the cardiac tissue. To do so, the energy per unit area component 510 may determine how many more conductive segments of the ground pad should be activated by the activation component 506 to achieve the desired energy per unit area. In embodiments, sensors on the tip of the catheter may send signals to the temperature component 514 included in the processing unit 500, which can then determine the temperature, of the environment surrounding the catheter's distal tip.

In embodiments, the processing unit 500 may include a display component 516. In embodiments, the display component 516 may determine the conductive segments that the activation component 506 has activated and output, to a display device (e.g., the display device 118 depicted in FIG. 1) a representation of the activated conductive segments.

FIGS. 6A-6D are illustrations depicting different activated sections of a segmented ground pad, in accordance with embodiments of the present disclosure. While FIGS. 6A-6D depict conductive segments that are arranged in Cartesian grid, as stated above in relation to FIGS. 4A-4B, the conductive segments may have other types of arrangements (e.g., the polar grid arrangement).

Figure 6A:
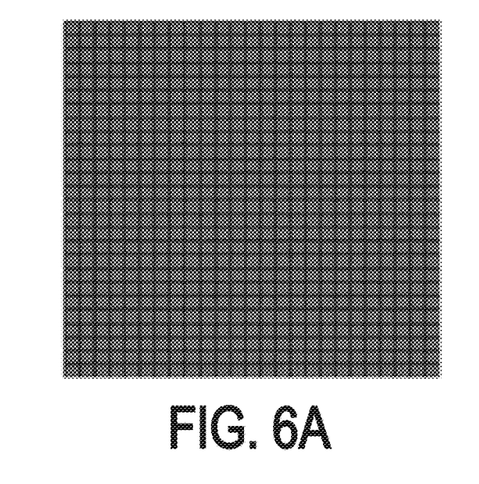
FIGS. 6A-6D are illustrations depicting different activated sections of a segmented ground pad, in accordance with embodiments of the present disclosure.
Figure 6B:
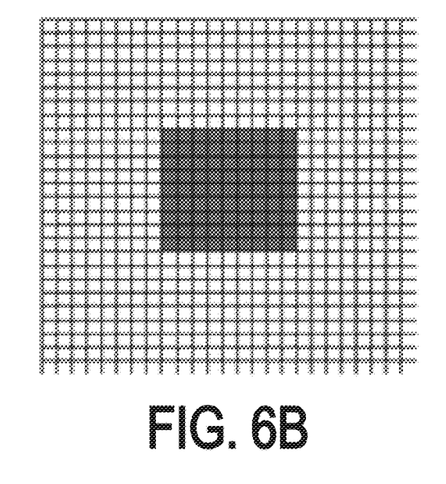
Figure 6C:
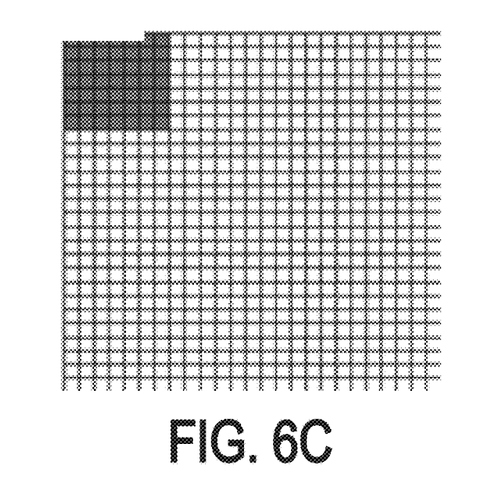
Figure 6D:
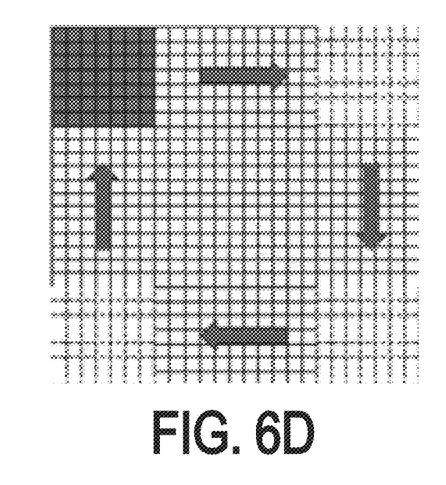

FIG. 6A depicts a segmented ground pad where all the conductive segments are activated. In embodiments, all the conductive segments may be activated so that the RF energy emitted by an ablation catheter is focused on a larger portion of cardiac tissue than if fewer conductive segments were activated. FIG. 6B depicts a segmented ground pad with a center portion of the conductive segments activated. In embodiments, a fewer portion of the conductive segments may be activated so that the RF energy emitted by an ablation catheter is focused on a smaller portion of cardiac tissue. FIG. 6C depicts a segmented ground pad with a corner portion of the conductive segments activated. In embodiments, a corner portion (or any other portion) of the conductive segments may be activated so that the conductive path from the ablation catheter to the ground pad is the path of shortest distance. FIG. 6D depicts a segmented ground pad where different portions of the conductive segments are being activated after one another. That is, the conductive segments that are activated and/or deactivated are changing and/or being updated. In embodiments, changing the conductive segments that are activated may be useful when the location of the catheter is changing.

Figure 7:
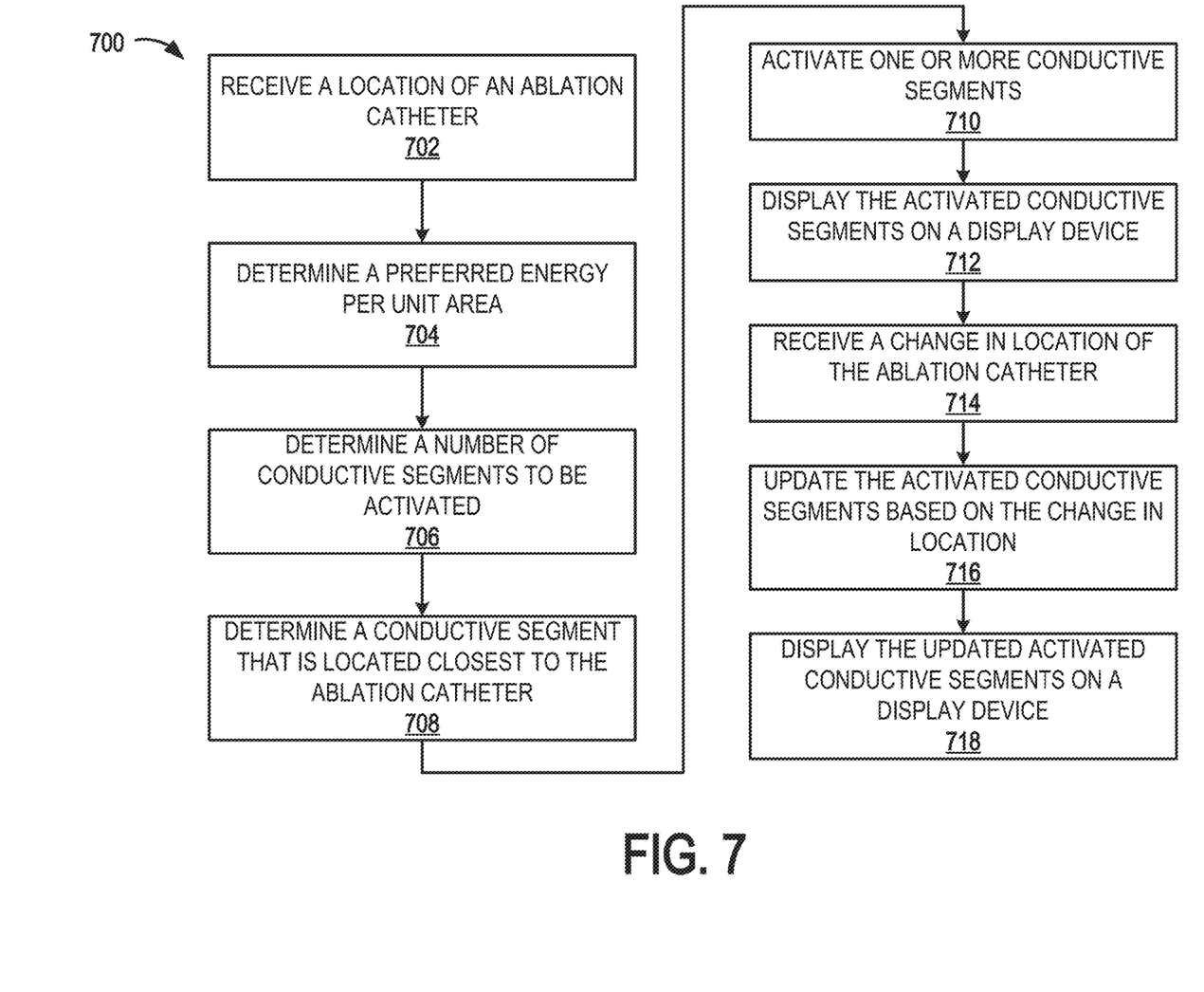
FIG. 7 is a flow diagram depicting an illustrative method for using a segmented ground pad, in accordance with embodiments of the present disclosure.

FIG. 7 is a flow diagram depicting an illustrative method 700 for using a segmented ground pad, in accordance with embodiments of the present disclosure. In embodiments, the method 700 includes receiving a location of an ablation catheter (block 702). In embodiments, a processing unit (e.g., the processing unit 116 depicted in FIG. 1 and/or the processing unit 500 depicted in FIG. 5) and/or a location component (e.g., the location component 508 depicted in FIG. 5) may receive a determine location of an ablation catheter from a tracking system (e.g., the tracking system 120 depicted in FIG. 1). In embodiments, the location of the catheter may be used to determine which conductive segments of a ground pad should be activated.

In embodiments, the method 700 also includes determining a preferred energy per unit area (block 704). In embodiments, a preferred energy per unit area may be determined by an energy per unit area component (e.g., the energy per unit area component 510 depicted in FIG. 5) to facilitate determining how many conductive segments of a ground pad should be activated (block 706), as described above in relation to FIG. 5. For example, fewer conductive segments may be activated at the beginning of a procedure, so that the RF energy is focused on a smaller portion of cardiac tissue; and, as the procedure continues, more conductive segments may be activated so that the RF energy is focused over a larger portion of cardiac tissue.

The method 700 may also include determining a conductive segment that is located closest to the tip of the ablation catheter (block 708). As described above, this may facilitate a conduction path, of RF energy, that has the shortest distance.

The method 700 also includes activating one or more conductive segments of the ground pad (block 710). In embodiments, the conductive segments may be activated by a switching apparatus (e.g., the switching apparatus 110 depicted in FIG. 1) via one or more wires (e.g., the wires 112 depicted in FIG. 1). Additionally or alternatively, the activated one or more segments may be based on a determined preferred energy per unit area, a determined number of conductive segments to be activated and/or a determined conductive segment that is located closest to the ablation catheter. In embodiments, the conductive segments that are activated may be displayed on a display device (e.g., the display device 118 depicted in FIG. 1).

In embodiments, the method 700 may also include receiving a change in location of the ablation catheter (block 714). The change in location of the ablation catheter may be due to movement of the ablation catheter, movement of the cardiac tissue due to pumping of the heart, movement of the patient and/or other perturbations that induce movement of the catheter. In embodiments, the change in the location of the catheter may be determined using a tracking system. Based on the received change in location, the conductive segments that are activated and/or deactivated may be changed or updated (block 716). After which, the updated activated and/or deactivated conductive segments may be displayed on a display device (block 718).

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

We claim:

1. A system comprising:
    a unitary ground pad comprising a plurality of conductive segments, wherein each conductive segment is capable of being independently activated;
    a plurality of conductive wires coupled to the plurality of conductive segments;
    a switching apparatus coupled to the plurality of conductive wires; and
    a processor coupled to the switching apparatus, wherein the processor is configured to:
        receive a location of the catheter's distal tip;
        determine at least one conductive segment that is located closest to the location of the catheter's distal tip;
        determine a preferred energy per unit area for a procedure;

determine a number of the plurality of conductive segments to be activated based upon the determined preferred energy per unit area; and send a signal to the switching apparatus to activate the determined number of conductive segments in order to provide a ground path for energy emitted by a catheter of an electrophysiology system, wherein the signal is based on the location of the catheter's distal tip and wherein locations of the activated conductive segments are approximately centered at the at least one determined conductive segment that is located closest to the location of the catheter's distal tip.

2. The system of claim 1, wherein the unitary ground pad comprises:

a reusable portion comprising a plurality of contacts, wherein each contact is configured to be removably coupled to a respective conductive segment; and a disposable portion comprising the plurality of conductive segments.

3. The system of claim 1, wherein the plurality of conductive segments are arranged in a grid array.

4. The system of claim 1, wherein the one or more activated conductive segments is a subset of the plurality of conductive segments.

5. The system of claim 1, wherein the received location of the catheter's distal tip comprises an orientation of the catheter's distal tip and a position of the catheter's distal tip.

6. The system of claim 1, wherein the processor is configured to:

receive a change in location of the catheter's distal tip; and send a signal to the switching apparatus to modify the one or more activated conductive segments based on the change in location of the catheter's distal tip.

7. The system of claim 1, wherein to determine a preferred energy per unit area, the processor is configured to:

determine an impedance sensed by the catheter; and
determine the preferred energy per unit area based on the determined impedance.

8. The system of claim 1, wherein to determine a preferred energy per unit area, the processor is configured to:

determine a temperature sensed by the catheter; and
determine the preferred energy per unit area based on the determined temperature.

9. A method comprising:

receiving a location of a catheter's distal tip of an electrophysiology system;

determining at least one conductive segment that is located closest to the location of the catheter's distal tip;

determining a preferred energy per unit area for a procedure;

determining a number of conductive segments of a plurality of conductive segments of a unitary ground pad array to be activated based upon the determined preferred energy per unit area; and activating the determined number of conductive segments to provide a ground path for energy emitted by the catheter, based on the location of the catheter's distal tip, wherein each conductive segment is capable of being independently activated and wherein locations of the activated conductive segments are approximately centered at the at least one determined conductive segment that is located closest to the location of the catheter's distal tip.

10. The method of claim 9, further comprising:
receiving a change in location of the catheter's distal tip; and updating the one or more activated conductive segments based on the change in location of the catheter's distal tip.

11. The method of claim 9, wherein determining a preferred energy per unit area comprises:

determining an impedance sensed by the catheter; and
determining the preferred energy per unit area based on the determined impedance.

12. A ground pad array system for use with an electrophysiology system, the ground pad array system comprising:

a unitary ground pad comprising a plurality of conductive segments, wherein each conductive segment is capable of being independently activated;

a plurality of conductive wires coupled to the plurality of conductive segments and a switching apparatus, wherein the switching apparatus is configured to activate a number of the plurality of conductive segments based upon a determined preferred energy per unit area for a procedure and a location of catheter's distal tip of the electrophysiology system, wherein the unitary ground pad provides a ground path for energy emitted by the catheter, in response to the activation of the number of conductive segments, and wherein locations of the activated conductive segments are approximately centered at one or more conductive segments that are located closest to the location of the catheter's distal tip.

13. The ground pad array system of claim 12, wherein the unitary ground pad comprises:

a reusable portion comprising a plurality of contacts, wherein each contact is configured to be removably coupled to a respective conductive segment; and a disposable portion comprising the plurality of conductive segments.

14. The ground pad array system of claim 12, wherein the plurality of conductive segments are arranged in a grid array.

* * * * *